United States Patent [19]

Zimmerman

[11] Patent Number: 5,254,737

[45] Date of Patent: * Oct. 19, 1993

[54] CONTINUOUS PREPARATION OF SECONDARY AMINES FROM NITRILES USING A TWO-STEP PROCESS

[75] Inventor: Robert L. Zimmerman, Austin, Tex.

[73] Assignee: Texaco Chemical Company, White Plains, N.Y.

[*] Notice: The portion of the term of this patent subsequent to Jul. 14, 2009 has been disclaimed.

[21] Appl. No.: 583,109

[22] Filed: Sep. 17, 1990

[51] Int. Cl.$^5$ .......................................... C07C 209/00
[52] U.S. Cl. .................... 564/490; 564/491; 564/493; 564/470
[58] Field of Search ................ 564/490, 491, 493, 470

[56] References Cited

U.S. PATENT DOCUMENTS

| | | | |
|---|---|---|---|
| 2,781,399 | 2/1957 | Shapiro | 260/583 |
| 2,811,556 | 10/1957 | Shapiro | 260/583 |
| 4,248,801 | 2/1981 | Tomidokoro et al. | 564/463 |
| 4,721,811 | 1/1988 | Sherwin et al. | 564/490 |

FOREIGN PATENT DOCUMENTS

| | | |
|---|---|---|
| 0021162 | 1/1981 | European Pat. Off. . |
| 0232097 | 8/1987 | European Pat. Off. . |
| 1180972 | 2/1970 | Fed. Rep. of Germany . |
| 0133229 | 12/1978 | German Democratic Rep. . |
| 836364 | 6/1960 | United Kingdom . |
| 1180972 | 2/1970 | United Kingdom . |
| 1323351 | 7/1973 | United Kingdom . |

OTHER PUBLICATIONS

Tomidokoro, S., et al., "Preparation of Long-Chain Secondary Amines by Reduction of Nitriles," *Chemical Abstracts*, 106:175777t, Japan Tokkyo Koho JP 62 00,901; 1987, p.671.

*Primary Examiner*—Allen J. Robinson
*Assistant Examiner*—Shailendra Kumar
*Attorney, Agent, or Firm*—James L. Bailey; Kenneth R. Priem; David L. Mossman

[57] ABSTRACT

A method for producing secondary amines, particularly fatty secondary amines such as ditallowamine from fatty nitriles, such as tallow nitrile over a reduction, hydrogenation catalyst, such as nickel or cobalt, in two steps has been discovered. The reaction gives high selectivity of secondary amine over the coproduced primary and tertiary amines. The first step of the reaction is conducted continuously in the presence of ammonia and hydrogen. The secondary amine proportion is increased by a second stage using the same catalyst as the first stage, but in the absence of ammonia.

11 Claims, No Drawings

CONTINUOUS PREPARATION OF SECONDARY AMINES FROM NITRILES USING A TWO-STEP PROCESS

CROSS-REFERENCE TO RELATED APPLICATION

The present application is related to U.S. patent application Ser. No. 07/506,747 filed Apr. 10, 1990 relating to the continuous preparation of secondary amines from nitriles using cobalt catalysts promoted with zirconium.

FIELD OF THE INVENTION

The invention relates to the production of secondary amines from nitriles, and, in one aspect, more particularly relates to the continuous production of secondary amines from nitriles using a single transition metal catalyst and two compatible processing steps.

BACKGROUND OF THE INVENTION

It has long been known that nitriles can be reduced to give amines. Typically a mixture of primary, secondary and tertiary amines are produced, and a common goal is to devise a process by which the result is a yield high in only one of the possible products; that is, has high selectivity to a particular product. The reaction is understood to proceed in two steps, and often the process is a two step process, usually using a different catalyst for the two steps. Frequently, the reaction is run as a batch reaction inasmuch as good selectivities have been difficult to achieve using continuous processes.

Particularly useful products from the reaction are the secondary amines. They have found such widespread uses as textile additives, disinfectants, antistatic agents, and organophilic ammonium bentonites. Especially useful are the unsaturated long-chain aliphatic secondary amines since the quaternary ammonium salts thereof can provide softness and antistaticity to various fabrics and hair, and can also be used as a softener for providing water absorbancy and handling ease to treated fabrics. The secondary amine ditallowamine is useful in the preparation of surfactants, but has never been continuously prepared in high selectivity from tallow nitrile. Tallow nitrile has sixteen to eighteen carbon atoms ($C_{16}$ to $C_{18}$).

Of particular interest is British Patent 1,180,972 (equivalent to Oberrauch, Hans, et al. "Secondary Fatty Amines", Chemical Abstracts, 70:11108n, West German Patent 1,280,243, 1969, p. 221) which teaches that aliphatic, saturated and unsaturated secondary fatty amines can be prepared by hydrogenation of the corresponding fatty acid nitrile by passing the nitrile at 140°-200° C. and 30-200 atm. of hydrogen together with water over a solid catalyst consisting of 20% copper, 0.8% chromium and 1% alkali metal with a wide-poured silica gel having a specific area of 250-350 m.$^3$/g as the support. See also British Patent 1,323,351 (equivalent to West German Auslegeschrift 1,941,290) which describes a process for making aliphatic saturated secondary amines from nitriles having 8 to 22 carbon atoms per molecule, where in a first step the starting product is hydrogenated to yield a mixture of saturated amines, and in a second step, this mixture is continuously desaminated (i.e., ammonia is split off) optionally with the addition of hydrogen, where each step is carried out in the presence of a fixed bed hydrogenation catalyst. The first step is conducted at a hydrogen pressure of from 100 to 300 atmospheres gauge and at a temperature in the range of from 100° to 200° C., while the second step is conducted at a pressure from 0 to 50 atmospheres and at a temperature in the range from 120° to 220° C. The catalysts used are a cobalt catalyst in the first step and then a copper catalyst; or alternatively a nickel catalyst in the first reaction and a cobalt catalyst in the second.

Tertiary monomethylamines having long chain alkyl groups are advantageously prepared from unsaturated aliphatic nitriles under a low pressure at a high yield by a three step process according to U.S. Pat. No. 4,248,801. The first step involves reducing nitriles with hydrogen in the presence of a nickel hydrogenation catalyst at 200° C. and under a hydrogen pressure of 0 through 10 kg/cm$^2$G, while the formed ammonia is removed.

Of lesser importance is the following group of publications, which includes U.S. Pat. No. 2,781,399, (equivalent to British Pat. 759,291) that teaches production of secondary aliphatic hydrocarbon amines via a batch reaction using a nickel hydrogenation catalyst. A similar process is described in U.S. Pat. No. 2,811,556, except that a copper oxide/chromium oxide catalyst is used.

Tomidokoro, S., et al., "Preparation of Long-Chain Secondary Amines by Reduction of Nitriles", Chemical Abstracts, 106:175777t, Japan Tokkyo Koho JP 62 00,901, 1987, p. 671, teaches the preparation of long-chain secondary amines by the reduction of aliphatic nitriles having 8 to 22 carbon atoms over nickel catalysts at 0-6 kg/cm$^2$ gauge and 200° to 230° C. while removing more that 85% formed NH$_3$. Thus, 250 g. of tallow nitrile was reduced over 0.5 g. Ni catalyst at 200°-300° C. and 5 kg/cm$^2$ while removing 93% formed NH$_3$ to give 240 g. of a mixture of primary (3.1%), secondary (91.1%) and tertiary amine (4.3%) amines.

European patent 0 021 162 B1 teaches the production of alkylamines with 12 to 22 carbon atoms by hydrogenating corresponding fatty nitriles in the presence of a nickel or cobalt catalyst. The hydrogen gas reactant is recirculated after removal of ammonia. The new feature is that throughout the reaction the water content of the circulating gas is adjusted to not above 5 g. per cubic meter, under practically zero-pressure conditions, before recycle. Additionally, a process for selectively preparing an unsaturated long-chain aliphatic secondary amine at a high yield involving reducing an unsaturated aliphatic nitrile having 8 to 22 carbon atoms or a nitrile mixture containing said nitrile with hydrogen in the presence of a nickel hydrogenation catalyst and a carboxylic acid amide at a reaction temperature of 160° to 200° C. is described in European Patent Application 0232097 A2.

A process for the selective production of aliphatic secondary amines from $C_{8-22}$ primary amines using dehydrogenation/hydrogenation catalysts is briefly mentioned in the English abstract to East German Application 133,229-A. In a first stage, the primary amine is dehydrogenated at normal pressure and at 170° to 260° C., by treatment with a inert gas (N$_2$) in an amount of 5 to 150 l/mol./h., for 30 to 60 minutes until a degree of conversion of the starting material of 85-98% is achieved. The resulting dehydrogenated product is then reacted with hydrogen at 100° to 140° C. and 0 to 50 atmospheres for 10 to 30 minutes to form the secondary amine. The nature of the catalyst was not mentioned in the abstract.

There remains a need for a continuous process for producing fatty secondary amines simply, and in high selectivities. Ideally, such a process would only use one catalyst.

SUMMARY OF THE INVENTION

Accordingly, it is an object of the present invention to provide a process for the continuous production of fatty secondary amines.

It is another object of the present invention to provide a continuous process for making fatty secondary amines that requires only one catalyst.

Another object of the invention is to provide a continuous process for producing fatty secondary amines in high selectivity.

In carrying out these and other objects of the invention, there is provided, in one form, a continuous process for the preparation of secondary amines from nitriles comprising a two-step process. First, a nitrile is continuously passed over a reduction, hydrogenation catalyst, in the presence of ammonia and hydrogen to produce an intermediate reaction product. Secondly, the intermediate reaction product is continuously passed over the same catalyst in the presence of hydrogen but the absence of ammonia.

DETAILED DESCRIPTION OF THE INVENTION

It has been discovered that secondary amines, particularly fatty secondary amines such as ditallowamine may be produced in high selectivity by passing the corresponding nitrile, such as tallow nitrile, over a reduction, dehydrogenation catalyst in two stages. The same catalyst may be used in both stages. The only difference between the two stages is that ammonia is not used in the second stage, whereby it is present, together with nitrogen, in the first stage.

The invention is particularly suited for producing fatty secondary amines from fatty nitriles, which are defined as having from about 8 to about 22 carbon atoms. A preferred feedstock because of its relative inexpensiveness is tallow nitrile which has from about 16 to 18 carbon atoms. The product from this feedstock is ditallowamine, also known as di(hydrogenated tallow)amine. Of course, the resulting secondary amine has twice the carbon atoms of the beginning nitrile.

As noted, the catalyst should be a reduction, hydrogenation-dehydrogenation catalyst, such as nickel, cobalt or the like. As will be shown, the inventive process is not limited to a particular hydrogenation catalyst and will work with many different catalysts. Nickel oxide and/or cobalt oxide may be used. Other suitable catalysts include cobalt metal and nickel metal, but, as noted, the process is not limited to these two materials. In one embodiment, promoters are used in conjunction with the hydrogenation catalyst. The promoters may include, but are not limited to, copper, chromium, zirconium and molybdenum, and the like, and mixtures thereof in forms such as copper oxide, chromium oxide, zirconium oxide and molybdenum oxide, for example. In one aspect, the proportion of the catalyst, such as cobalt or nickel should range from about 30 to about 70%, preferably from about 40 to about 60%. The promoters, such as copper, chromium, zirconium and molybdenum in oxide form as examples only, should be present in an amount great enough to give a promotive effect. In one aspect, the amount of promoter may range from about 1 to about 18%, more preferably from about 5 to about 12%. In one embodiment, the metal composition is present in about a 50 wt. % proportion.

In another embodiment of the invention, the metal compositions are supported. The catalyst may be supported upon kieselguhr, also known as diatomaceous earth, diatomite and infusorial earth. The catalyst may also be supported on materials including, but not limited to, alumina, silica or titania.

The reaction is preferably conducted at elevated temperatures and pressures. For example, the temperature may range from about 100° to about 200° C., preferably from about 130° to about 180° C. The pressure may range from about 50 to about 5000 psig, and more preferably range from about 200 to about 1000 psig. It is preferred that ammonia and hydrogen are present during the first step of the reaction. A solvent, such as cyclohexane for example only, may optionally be employed in the reaction. Other suitable inert solvents may include, but are not limited to, straight, branched and cyclic alkanes having up to about twelve carbon atoms.

The reaction is conducted in two steps. It has been surprisingly discovered if the reaction is conducted in two continuous stages that ammonia is preferably not present in the second stage; whether using a nickel catalyst, a cobalt catalyst, or other hydrogenation-dehydrogenation catalyst. The absence of ammonia in the second step is desired since primary amines are formed in the first reaction, and the production of the secondary amines from two primary amines in the second step also produces an ammonia molecule. Thus, the absence of ammonia in the second step would facilitate the second reaction. Surprisingly, it was also discovered that the same catalyst may be used even if with this two-step process.

The use of a continuous reaction has advantages over the batch reactions in that no filtration or loss of catalyst is experienced, since a fixed bed is used in the continuous reaction. The invention will be illustrated in greater detail with reference to the following examples. All analyses were performed by wet chemistry (titration) in a manner similar to, if not identical to, ASTM methods for determining tallow amines.

EXAMPLE 1

Single Pass Using a Co-Zr Catalyst on Kieselguhr

A tubular reactor filled with 430 cc of catalyst was used for the reaction. The catalyst was cobalt oxide promoted with zirconium oxide supported on kieselguhr. The pressure was 500 psig. The products resulting at various reaction temperatures and feed rates are given in Table I.

TABLE I

Product Analyses for Example 1

| Temp. °C. | Feed Rate, Tallow Nitrile, lb/hr. | Feed Rate, NH$_3$, lb/hr. | Feed Rate, H$_2$, l/hr. | Product Primary Amine, % | Product Secondary Amine, % | Product Tertiary Amine, % |
|---|---|---|---|---|---|---|
| 170 | 0.75 | 0.06 | 355 | 34.8 | 61.8 | 3.6 |
| 180 | 0.75 | 0.06 | 355 | 44.3 | 50.7 | 4.9 |
| 190 | 0.75 | 0.06 | 355 | 19.4 | 73.6 | 7.0 |
| 170 | 0.69 | 0.12 | 355 | 25.6 | 72.3 | 2.1 |
| 180 | 0.69 | 0.12 | 355 | 20.5 | 76.5 | 2.9 |
| 190 | 0.69 | 0.12 | 355 | 17.2 | 76.0 | 6.9 |

EXAMPLE 2

Double Pass Using a Co-Zr Catalyst on Kieselguhr

The same reactor, catalyst and pressure were used for this Example as were used in Example 1. In this Example, two passes were used instead of only a single pass. In the first pass, ammonia was used, while in the second pass, no ammonia was used. The results, feed rates and temperatures are given in Table II.

TABLE II

Product Analyses for Example 2

| Pass | Temp., °C. | Feed Rate, Tallow Nitrile, lb/hr. (crude ditallow amine) | Feed Rate, NH$_3$, lb/hr. | Feed Rate, H$_2$, l/hr. | Primary amine, % | Secondary amine, % | Tertiary amine, % |
|---|---|---|---|---|---|---|---|
| 1st | 175 | 0.69 | 0.12 | 355 | 35.9 | 61.7 | 2.4 |
| 2nd | 150 | 0.75 | 0 | 355 | 2.2 | 92.6 | 5.2 |

As can be seen in Examples 1 and 2, two passes give much higher secondary amine than can be obtained in one pass; compare 92.6% with 76.6%.

EXAMPLE 3

Single Pass Using a Ni-Cu-Cr Catalyst

A tubular reactor filled with 600 cc of catalyst was used for the reaction. The catalyst was a conventional nickel-copper-chromium catalyst. The pressure was 500 psig. The products resulting at various reaction temperatures are given in Table III.

TABLE III

Product Analyses for Example 3

| Temp. °C. | Feed Rate, Tallow Nitrile + Cyclohexane, lb/hr. | Feed Rate, NH$_3$, lb/hr. | Feed Rate, H$_2$, l/hr. | Primary Amine, % | Secondary Amine, % | Tertiary Amine, % |
|---|---|---|---|---|---|---|
| 130 | 0.85 | 0.06 | 387 | 54.4 | 44.7 | 1.2 |
| 140 | 0.85 | 0.06 | 387 | 43.8 | 54.0 | 2.3 |
| 150 | 0.85 | 0.06 | 387 | 33.2 | 63.2 | 3.3 |
| 160 | 0.85 | 0.06 | 387 | 23.2 | 69.8 | 7.0 |
| 170 | 0.85 | 0.06 | 387 | 18.7 | 69.2 | 12.1 |
| 180 | 0.85 | 0.06 | 387 | 12.8 | 70.3 | 16.9 |

EXAMPLE 4

Double Pass Using a Ni-Cu-Cr Catalyst

The same reactor, catalyst and pressure were used for this Example as were used in Example 3. In this Example, two passes were used instead of only a single pass. As before, the product from the first pass is used as the feed for the second pass, in which no ammonia is used. The product results are shown in Table IV.

TABLE IV

Product Analyses for Example 4

| Pass | Temp. °C. | Tallow Nitrile, + Cyclohexane, lb/hr. | Cyclohexane, lb/hr. | From 1st pass, lb/hr. | NH$_3$, lb/hr. | H$_2$, l/hr. | 1° amine, % | 2° amine, % | 3° amine, % |
|---|---|---|---|---|---|---|---|---|---|
| 1st | 140 | 0.85 | — | — | 0.06 | 387 | 44.6 | 53.6 | 1.9 |
| 2nd | 185 | — | 0.73 | 0.36 | 0 | 387 | 11.3 | 83.0 | 5.7 |

The ratio of cyclohexane to tallow nitrile in the first pass was 2:1. Again, by using two passes, with the second pass not using ammonia, higher secondary amine yield can be achieved than by using a single pass; compare 83% from Example 4 with 70.3% from Example 3.

EXAMPLE 5

Single Pass Using a Ni-Cu-Cr-Mo Catalyst

A tubular reactor filled with 600 cc of catalyst was used for the reaction. The catalyst was the nickel-copper-chromium-molybdenum catalyst used in Example 1.

The pressure was 500 psia and the hydrogen feed rate was 387 l/hr.. The products resulting at various reaction temperatures are given in Table V.

TABLE V

Product Analyses for Example 5

| Temp. °C. | Feed Rate, Tallow Nitrile, lb/hr. | Feed Rate, Cyclohexane, lb/hr. | Feed Rate, NH$_3$, lb/hr. | Product Primary Amine, % | Secondary Amine, % | Tertiary Amine, % |
|---|---|---|---|---|---|---|
| 120 | 0.28 | 0.57 | 0.06 | 71.7 | 27.6 | 0.7 |
| 130 | 0.28 | 0.57 | 0.06 | 68.5 | 31.1 | 0.4 |
| 140 | 0.28 | 0.57 | 0.06 | 50.4 | 48.8 | 0.8 |
| 150 | 0.28 | 0.57 | 0.06 | 24.5 | 73.6 | 1.8 |
| 160 | 0.28 | 0.57 | 0.06 | 13.5 | 81.7 | 4.8 |
| 170 | 0.28 | 0.57 | 0.06 | 10.6 | 78.4 | 11.1 |
| 180 | 0.28 | 0.57 | 0.06 | 11.6 | 65.3 | 23.2 |

EXAMPLE 6

Double Pass Using a Ni-Cu-Cr-Mo Catalyst

The same reactor, catalyst, hydrogen feed and pressure were used for this Example as were used in Example 5. In this Example, two passes were used instead of only a single pass. As before, the product from the first pass is used as the feed for the second pass, in which no ammonia is used. The product results are shown in Table VI.

TABLE VI

Product Analyses for Example 6

| Pass | Temp. °C. | Tallow Nitrile, lb/hr. | Cyclohexane, lb/hr. | NH$_3$, lb/hr. | Crude Product from 1st pass, lb/hr. | Product 1° amine, % | 2° amine, % | 3° amine, % |
|---|---|---|---|---|---|---|---|---|
| 1st | 155 | 0.28 | 0.57 | 0.06 | — | 50.6 | 48.6 | 0.9 |
| 2nd | 160 | — | 0.72 | 0 | 0.36 | 4.5 | 93.2 | 2.3 |

Again, much higher secondary amine yield was achieved by using two passes instead of one; compare 93.2% from Example 6 with the highest yield of 81.7% in Example 5.

Such excellent results in the continuous production of ditallowamine from tallow nitrile using a single catalyst are unknown in the art. Many modifications may be made in the process of this invention without departing from the spirit and scope thereof which are defined only in the appended claims. For example, one skilled in the art may discover that particular reaction conditions or sequences, relative flow rates, or catalyst, which may not be explicitly recited herein, but which are nevertheless anticipated, would give desirable results.

I claim:

1. A continuous process for the preparation of secondary amines from nitriles comprising the steps of:
    continuously passing a nitrile over a reduction, hydrogenation catalyst, in the presence of added ammonia and hydrogen to produce an intermediate reaction product; and
    continuously passing the intermediate reaction product over the same catalyst in the presence of hydrogen but the absence of ammonia.

2. The process of claim 1 where the process is carried out at a temperature in the range of about 100° to about 200° C. and a pressure in the range of about 50 to about 5000 psig.

3. The process of claim 1 where the reduction, hydrogenation catalyst is selected from the group consisting of cobalt and nickel catalysts.

4. The process of claim 3 where the catalyst is at least 30% cobalt or nickel oxide and at least 1% of a promoter.

5. The process of claim 1 where the nitrile has from 8 to 22 carbon atoms.

6. A continuous process for the preparation of secondary amines from nitriles comprising the steps of:
    continuously passing a nitrile having 8 to 22 carbon atoms over a reduction, hydrogenation catalyst in the presence of added ammonia and hydrogen to produce an intermediate reaction product; and
    continuously passing the intermediate reaction product over the same catalyst in the presence of hydrogen but the absence of ammonia;
    where the process is carried out at a temperature in the range of about 100° to about 200° C. and a pressure in the range of about 50 to about 5000 psig.

7. The process of claim 6 where the reduction, hydrogenation catalyst is selected from the group consisting of cobalt and nickel catalysts.

8. The process of claim 7 where the catalyst is at least 30% cobalt or nickel oxide and at least 1% of a promoter.

9. The process of claim 6 conducted in the absence of an additional catalyst.

10. A continuous process for the preparation of secondary amines from nitriles comprising the steps of:
    continuously passing a nitrile having 8 to 22 carbon atoms over a reduction, hydrogenation catalyst selected from the group consisting of cobalt and nickel catalysts, containing at least 30% cobalt or nickel in the presence of added ammonia and hydrogen, to produce an intermediate reaction product; and
    continuously passing the intermediate reaction product over the same catalyst in the presence of hydrogen but the absence of ammonia and in the absence of an additional catalyst,
    where the process is carried out at a temperature in the range of about 100° to about 200° C. and a pressure in the range of about 50 to about 5000 psig.

11. The process of claim 10 where the catalyst also contains at least 1% of a promoter.

* * * * *